US012788834B2

United States Patent

(12) United States Patent
Mcluckie et al.
(10) Patent No.: US 12,788,834 B2
(45) Date of Patent: Nov. 10, 2026

(54) SELF-CLEANING DOMESTIC APPLIANCE

(71) Applicant: Dyson Technology Limited, Wiltshire (GB)

(72) Inventors: Gemma Mcluckie, Poole (GB); Dennis Mathews, Bristol (GB); Nikian Naji Aghababaie, London (GB)

(73) Assignee: Dyson Technology Limited, Malmesbury (GB)

( * ) Notice: Subject to any disclaimer, the term of this patent is extended or adjusted under 35 U.S.C. 154(b) by 535 days.

(21) Appl. No.: 18/028,112

(22) PCT Filed: Sep. 22, 2021

(86) PCT No.: PCT/GB2021/052465
§ 371 (c)(1),
(2) Date: Mar. 23, 2023

(87) PCT Pub. No.: WO2022/069874
PCT Pub. Date: Apr. 7, 2022

(65) Prior Publication Data

US 2023/0321290 A1 Oct. 12, 2023

(30) Foreign Application Priority Data

Sep. 30, 2020 (GB) ..................................... 2015468

(51) Int. Cl.
*A61L 2/084* (2026.01)
*A45D 20/12* (2006.01)
(Continued)

(52) U.S. Cl.
CPC .............. *A61L 2/084* (2013.01); *A45D 20/12* (2013.01); *A61L 2/24* (2013.01);
(Continued)

(58) Field of Classification Search
CPC ....................................................... A61L 2/084
See application file for complete search history.

(56) References Cited

U.S. PATENT DOCUMENTS 6,094,767 A 8/2000 Keiji
8,973,284 B2 3/2015 Shami et al.
(Continued)

FOREIGN PATENT DOCUMENTS

AU 2011265411 A1 7/2012
CN 201870566 U 6/2011
(Continued)

OTHER PUBLICATIONS

International Search Report and Written Opinion received for PCT Patent Application No. PCT/GB2021/052438, mailed on Nov. 29, 2021, 8 pages.
(Continued)

*Primary Examiner* — Kevin Joyner
(74) *Attorney, Agent, or Firm* — Tucker Ellis LLP; Michael G. Craig

(57) ABSTRACT

A docking station is provided for holding at least a part of a domestic appliance and for decontaminating the at least one nozzle thereof. The domestic appliance is provided including an air inlet, an air outlet with at least one nozzle, and a compressor configured to compress incoming air received at the inlet and to expel the compressed air through the at least one nozzle. The domestic appliance further includes at least one light source for emitting light in a violet portion of the visual spectrum, the at least one light source being arranged in such a way as to illuminate the at least one nozzle for the decontamination thereof.

20 Claims, 9 Drawing Sheets

(51) Int. Cl.
*A61L 2/24* (2006.01)
*F24F 8/108* (2021.01)

(52) U.S. Cl.
CPC ..... *A45D 2020/126* (2013.01); *A61L 2202/11* (2013.01); *A61L 2202/14* (2013.01); *F24F 8/108* (2021.01); *F24F 2221/22* (2013.01)

(56) References Cited

U.S. PATENT DOCUMENTS

| | | | | |
|---|---|---|---|---|
| 10,894,104 | B1 | 1/2021 | Kim et al. | |
| 2010/0170104 | A1 | 7/2010 | Shami et al. | |
| 2011/0286883 | A1 | 11/2011 | Hecht et al. | |
| 2014/0077398 | A1 | 3/2014 | Staniforth et al. | |
| 2017/0321877 | A1 | 11/2017 | Polidoro | |
| 2018/0178823 | A1 | 6/2018 | Yang et al. | |
| 2019/0167833 | A1 | 6/2019 | Yang et al. | |
| 2019/0247528 | A1 | 8/2019 | Rodriguez | |
| 2019/0368180 | A1 | 12/2019 | Yaoka et al. | |
| 2020/0000301 | A1 | 1/2020 | Morin et al. | |
| 2020/0197549 | A1 | 6/2020 | Mancinelli et al. | |
| 2020/0206373 | A1* | 7/2020 | Winslow | A23B 2/53 |
| 2020/0298162 | A1 | 9/2020 | Jeon et al. | |
| 2020/0298169 | A1 | 9/2020 | Jeon et al. | |
| 2021/0031244 | A1 | 2/2021 | Jang et al. | |
| 2021/0046198 | A1* | 2/2021 | Winslow | A61L 2/084 |
| 2023/0330285 | A1 | 10/2023 | Mcluckie et al. | |
| 2023/0330293 | A1 | 10/2023 | Stringer et al. | |
| 2023/0337875 | A1 | 10/2023 | Stringer et al. | |

FOREIGN PATENT DOCUMENTS

| | | | |
|---|---|---|---|
| CN | 102448345 | A | 5/2012 |
| CN | 103479296 | A | 1/2014 |
| CN | 103479298 | A | 1/2014 |
| CN | 103480015 | A | 1/2014 |
| CN | 106998764 | A | 8/2017 |
| CN | 107568875 | A | 1/2018 |
| CN | 209146972 | U | 7/2019 |
| CN | 209982181 | U | 1/2020 |
| CN | 111067428 | A | 4/2020 |
| CN | 111380180 | A | 7/2020 |
| CN | 111720908 | A | 9/2020 |
| DE | 4206190 | A1 | 5/1993 |
| EP | 2468167 | A2 | 6/2012 |
| EP | 3453302 | A2 | 3/2019 |
| EP | 3575503 | A1 | 12/2019 |
| EP | 3712520 | A1 | 9/2020 |
| EP | 3712521 | A1 | 9/2020 |
| EP | 3771395 | A1 | 2/2021 |
| GB | 2500011 | A | 9/2013 |
| JP | 2002292226 | A | 10/2002 |
| JP | 2005-040351 | A | 2/2005 |
| JP | 2005-040352 | A | 2/2005 |
| JP | 2005-124861 | A | 5/2005 |
| JP | 2006-274573 | A | 10/2006 |
| JP | 2010207278 | A | 9/2010 |
| JP | 2010-227466 | A | 10/2010 |
| JP | 2010-268941 | A | 12/2010 |
| JP | 2012-245218 | A | 12/2012 |
| JP | 2013172834 | A | 9/2013 |
| JP | 2019217206 | A | 12/2019 |
| KR | 10-2006-0027207 | A | 3/2006 |
| KR | 10-2010-0090549 | A | 8/2010 |
| KR | 10-2011-0042990 | A | 4/2011 |
| KR | 10-1110302 | B1 | 2/2012 |
| KR | 10-1185270 | B1 | 9/2012 |
| KR | 10-2014-0047432 | A | 4/2014 |
| KR | 10-2015-0006525 | A | 1/2015 |
| KR | 10-1507922 | B1 | 4/2015 |
| KR | 10-2017-0049041 | A | 5/2017 |
| KR | 10-1897245 | B1 | 9/2018 |
| KR | 10-2035556 | B1 | 10/2019 |
| KR | 10-2020-0033117 | A | 3/2020 |
| KR | 10-2020-0084157 | A | 7/2020 |
| WO | 2005/074776 | A1 | 8/2005 |
| WO | 2022/069869 | A1 | 4/2022 |

OTHER PUBLICATIONS

International Search Report and Written Opinion received for PCT Patent Application No. PCT/GB2021/052462, mailed on Dec. 23, 2021, 8 pages.

International Search Report and Written Opinion received for PCT Patent Application No. PCT/GB2021/052463, mailed on Jan. 5, 2022, 8 pages.

International Search Report and Written Opinion received for PCT Patent Application No. PCT/GB2021/052464, mailed on Dec. 14, 2021, 9 pages.

International Search Report and Written Opinion received for PCT Patent Application No. PCT/GB2021/052465, mailed on Jan. 5, 2022, 10 pages.

Examination Report received for GB Application No. 2015466.2, mailed on Jan. 25, 2023, 1 page.

Examination Report received for GB Application No. 2015466.2, mailed on May 15, 2023, 2 pages.

Search Report received for GB Application No. 2015464.7, mailed on Mar. 24, 2021, 1 page.

Search Report received for GB Application No. 2015466.2, mailed on Feb. 19, 2021, 2 pages.

Search Report received for GB Application No. 2015468.8, mailed on Mar. 15, 2021, 2 pages.

Search Report received for GB Patent Application No. 2015463.9, mailed on Mar. 23, 2021, 1 page.

* cited by examiner

SELF-CLEANING DOMESTIC APPLIANCE

RELATED APPLICATION DATA

This application is the National Stage of International Application No. PCT/GB2021/052465 filed Sep. 22, 2021, and claims benefit of United Kingdom Application No. 2015468.8 filed Sep. 30, 2020, each of which are herein incorporated by reference in their entirety.

TECHNICAL FIELD

The present invention relates to a docking station for such a domestic appliance, and to a combination of a domestic appliance and the docking station.

BACKGROUND

Examples of such domestic appliances are cooling fans, air purifiers and hair dryers. They all draw in air from the environment through an inlet and use a compressor to subsequently and forcibly expel the air through a nozzle or a plurality of nozzles. Depending on the application, the air may be filtered, cooled, heated, moisturised, dried, or otherwise treated, while it flows between inlet and outlet. The nozzles direct the expelled air directly to the user or into a room or environment where the user is residing.

A problem with such domestic appliances is that the air drawn in at the inlet, is obtained from an environment that may contain all kinds of contamination. Larger dirt and dust particles may be filtered out, but smaller contaminants such as bacteria and other microbes are drawn in too. Such microbial contamination may then be directly blown towards the user or may gather and grow around the nozzles, in the filters, or elsewhere inside the air ducts of the domestic appliance. When users frequently get into direct contact with the nozzles, e.g. with hair dryers or wearable devices, contamination may also occur due to such direct contact. Use of the same appliance by different persons will further increase the health and safety risks associated with such contamination.

Cleaning of the domestic appliance will often be done with a wet cloth, which will likely lead to more microbial contamination, rather than less. As a consequence, there is a need for ways to better protect the users of vacuum cleaners against contact with unwanted microbes while cleaning their homes and offices.

SUMMARY OF THE INVENTION

According to a first aspect of the invention, a docking station is provided for a domestic appliance, the domestic appliance comprising an air outlet with at least one nozzle. The docking station comprises a docking bay for receiving and holding at least a part of the domestic appliance, and a docking sensor for providing a docking signal when the domestic appliance is held in the docking bay. The docking station further comprises at least one light source for emitting light in a violet portion of the visual spectrum, the at least one light source being arranged in such a way as to illuminate the at least one nozzle by emitting the light while the domestic appliance is being held in the docking bay. A docking station controller is operatively coupled to the docking sensor and the at least one light source and operative to receive the docking signal and to execute, in response thereto, a decontamination program, the decontamination program including using the at least one light source to illuminate the at least one nozzle for the decontamination thereof.

Docking stations are typically provided for smaller portable domestic appliances such as hair dryers and small desk fans. Battery powered domestic appliances need to be charged after having been used for some amount of time. While the batteries can be charged by just plugging in a power cable, docking stations may add additional functionality. A docking station may provide a safe and convenient way to store the device when it is not being used, possibly together with some of its accessories that are only used for selected modes of operation. The docking station may comprise control electronics for managing the charging process and informing the user about its progress. According to this aspect of the invention, the docking station is further capable of decontaminating the at least one nozzle or other parts of the domestic appliance. Decontaminating parts of the domestic appliance while being docked brings the advantage that the decontamination does not use any battery power that could otherwise have been used for the primary function of the device.

The amount of time needed for fully decontaminating the contaminated parts will generally be of the same order as the time needed for charging the batteries. When, e.g., using low intensity 405 nm LED light, illumination times of 30 minutes to a few hours may be needed for getting rid of most of the microbes. This decontamination process can thus be performed while the domestic appliance is out of operation anyhow. Furthermore, by integrating the light source in the docking station and decontaminating the parts when the domestic appliance is docked, it is ensured that the decontamination process does not drain the batteries. Yet another advantage is that this functionality can easily be added to an existing domestic appliance by only replacing or upgrading the docking station, and without having to replace the whole device.

The docking station may be designed to receive the domestic appliance as a complete unit or only separable parts of the device that need to be decontaminated or charged. The docking station may comprise multiple docking bays for receiving different parts and accessories of the device. For example, the docking station may comprise a docking bay for a hair dryer that is charged and decontaminated when its presence is detected. A second docking bay may be provided for receiving an accessory comprising nozzles. The light source for illuminating the nozzles of the accessory may be switched on when the charging starts and/or when the placement of the accessory is detected. In another example, the docking station is configured to receive a filter unit of an air purifier. The light source is switched on when a presence of the filter unit is detected. Such a docking station can be used for decontaminating the filter units of multiple air purifiers owned by the same user.

In an embodiment, the docking station further comprises a communication unit, operatively coupled to the docking station controller, for enabling communication between the docking station controller and an appliance controller of the domestic appliance. Such a communication unit may, e.g., be used for receiving information from various sensors of the domestic appliance, or for receiving specific instructions from a controller of that device. Further, the communication unit may send similar sensor signals and/or instructions to the controller of the domestic appliance.

According to one more aspect of the invention, a combination is provided of a docking station and a domestic appliance as described above. As indicated before, the light source and the control thereof may be located in the docking station, in the domestic appliance or in a combination of both. Preferably, the docking station and the domestic appliance each comprise a communication unit for enabling communication between the docking station controller and an appliance controller of the domestic appliance. The domestic appliance may comprise a light guide, arranged to guide the emitted light from the at least one light source of the docking station to the at least one nozzle of the domestic appliance. Similarly, a filter of the domestic appliance for filtering the incoming air may be illuminated by the light source of the docking station, either directly or via a light guide.

According to an aspect there is provided a domestic appliance comprising an air inlet, an air outlet with at least one nozzle, and a compressor configured to compress incoming air received at the inlet and to expel the compressed air through the at least one nozzle. The domestic appliance further comprises at least one light source for emitting light in a violet portion of the visual spectrum, the at least one light source being arranged in such a way as to illuminate the at least one nozzle for the decontamination thereof. The domestic appliance may, for example, be a fan, an air purifier, a hair dryer, or a wearable device.

The violet portion of the visual spectrum is typically defined as spanning the range of about 380 to 450 nm. The light used may thus, e.g., have a wavelength of about 405 nm. Light of these wavelengths is known to be very effective in killing any microbes that may have accumulated on the illuminated surfaces. Although such light is known to be used in light fixtures used for cleaning rooms in hospitals and in standalone curing lights used for 3D printer resin and nail polish, it has so far not been used in airflow generating domestic appliances or for cleaning contaminated parts of such devices. The use of violet visible light for this particular implementation brings a number of advantages that are not found in UV or near UV light. For example, the low energy visible light does not damage the material of the surfaces it illuminates. This is especially advantageous because most domestic appliances are at least partially made of plastics that are easily damaged by UV light. Another important advantage of the violet visible light is that no direct line of sight between the light source and the surface or part to be cleaned is needed. Indirect irradiation of the violet visible light helps to get rid of the microbial contamination too.

It is to be noted that emitting light in a violet portion of the visual spectrum as part of a decontamination process means that the emitted light contains a significant portion of light in that part of the electromagnetic spectrum and that the intensity of that significant portion is sufficient to have a useful anti-microbial and decontaminating effect. The emitted light does not need to be exclusively in the violet portion of the visual spectrum. As long as there is a sufficient intensity of light in that portion of the spectrum, and preferably at or around the 405 nm wavelength, for achieving a decontaminating effect, light of other parts of the electromagnetic spectrum may be emitted too. Further it is noted that, as part of the decontamination process, the intensity of the emitted light may vary over time. Such variations may be gradual and continuous or in the form of a pattern of light pulses. If pulsed light is used, the frequency, duration and intensity of the pulses may either be constant or varying.

The at least one light source may be active whenever the domestic appliance is connected to an external power source. However, if the emitted light is visible for the user, a time-controlled operation of the at least one light source may be preferred. For battery powered devices too, an always-on strategy may not be optimal. The domestic appliance may therefor comprise a controller, operatively coupled to and configured for timed control of the at least one light source. The controller may, e.g., be configured to activate the at least one light source in response to activation of a decontamination button. This allows the user to start and end the decontamination process at will. However, to ensure that the device is decontaminated regularly, some form of automatic or semi-automatic control may be preferred.

The controller is operatively coupled to the compressor and configured to activate the at least one light source during a decontamination period, a start and/or a duration of the decontamination period depending on an on/off state of the compressor. While the use of violet visible light is found to be an effective way to eliminate microbial contamination, it is a time-consuming process. When, e.g., using low intensity 405 nm LED light, illumination times of 30 minutes to a few hours may be needed for getting rid of most of the microbes. During use, the critical parts (nozzles, filters) are likely to be contaminated faster than the light source can prevent. Decontaminating during use may therefore not be very useful or energy efficient. However, when the compressor is switched off, a decontamination program can start. A short delay may be built in to ensure that the device is really not in use and not just switched off for a very short period of time.

If the domestic appliance is battery powered, the at least one light source may be activated when the domestic appliance is connected to a battery charger. This avoids the battery pack of the domestic appliance being drained by the decontamination process and making it incapable of performing its primary function. Activation and deactivation of the at least one light source may further depend on a charging state of the battery, for example by only activating the light source when connected to the battery charger or when still being charged to at least 50% of its full battery capacity. Charging the battery pack may be done by simply connecting a power cable to a charger circuit. Alternatively, the batteries are charged when placing the domestic appliance, or a battery containing part thereof, into a docking station that is provided for that purpose.

The domestic appliance may comprise a light guide, arranged to guide the emitted light from the at least one light source to the at least one nozzle. This may be especially useful in a domestic appliance with a plurality of nozzles. For example, optical fibres or light guides of transparent or semi-transparent plastics may guide the emitted light from a central light source to the remotely located nozzles, thereby obviating the need for separate light sources being provided with each nozzle. The light guide may further help to illuminate other internal parts of the domestic appliance that may be susceptible to microbial contamination.

Optionally, the domestic appliance further comprises a filter for filtering the incoming air, the at least one light source being arranged in such a way as to illuminate the filter. The filter may be located upstream or downstream of the compressor. Like the nozzles, the filter may be illuminated directly by the light source or via a light guide.

BRIEF DESCRIPTION OF THE DRAWINGS

Embodiments of the invention will now be described by way of example with reference to the accompanying drawings, in which.

DETAILED DESCRIPTION

Figure 1:
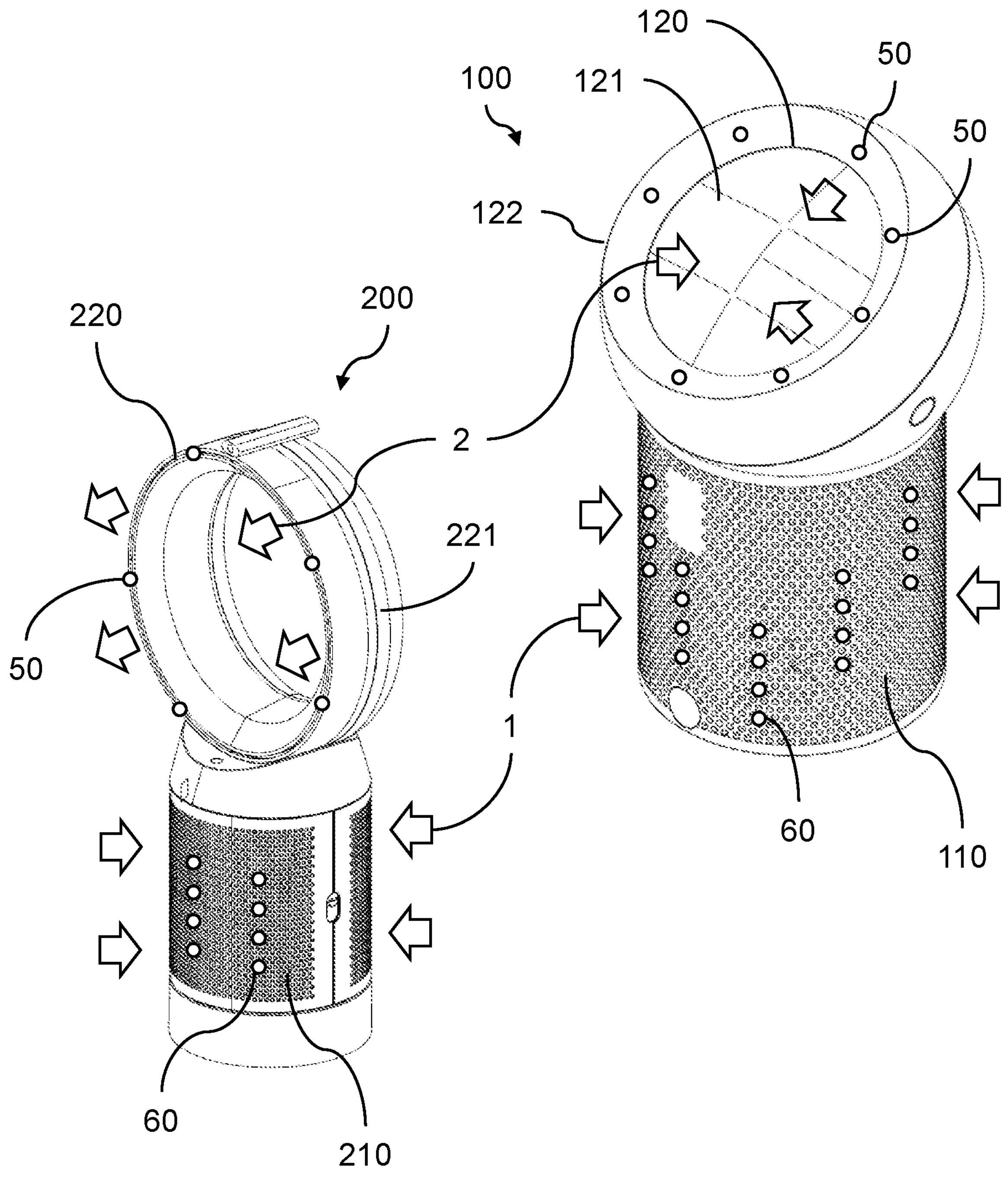
FIG. 1 shows two air fans according to embodiments of the invention.
Figure 2:
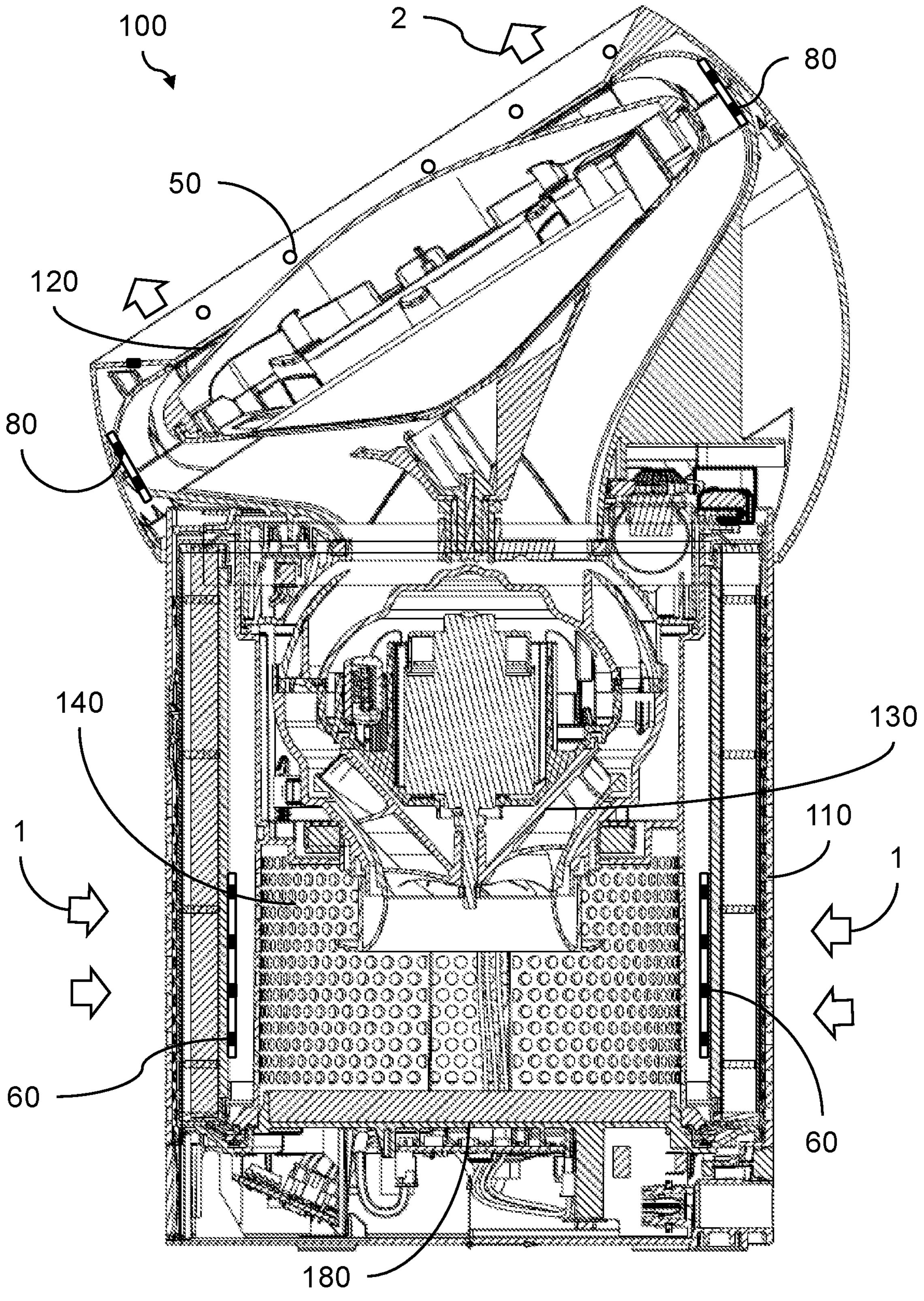
FIG. 2 shows a cross section of one of the air fans of FIG. 1.

FIG. 1 shows two air fans 100, 200 according to embodiments of the invention. FIG. 2 shows a cross section of one of the air fans 100 of FIG. 1. Incoming air 1 enters the air fans 100, 200 through an air inlet 110, 210 in the pedestals, of the air fans 100, 200. The air inlets 110, 210 in these air fans 100, 200 are formed by perforated metal plates, but other types of air inlets may be equally suitable. Inside the pedestals, a compressor 130 is provided for compressing the incoming air 1 and blowing the air towards and out through a nozzle 120, 220. In the air fan 100 on the right side of FIG. 1, the nozzle 120 is provided between an inner core 121 and an outer shell 122 of a largely spherical output unit that rests on top of the pedestal. In the air fan 200 on the left side of FIG. 1, the nozzle 220 is provided at an annular end surface of a ring-shaped output unit 221 that rests on top of the pedestal. The air fans 100, 200 in this example are equipped with filters 140 for purifying the incoming air 1 before it is released through the nozzles 110. Therefore, these air fans 100, 200 are also called air purifiers 100, 200.

The air purifiers 100, 200 further comprise multiple light sources 50, 60 for emitting light in a violet portion of the visual spectrum. For example, the light sources may be LEDs 50, 60 having a wavelength of 405 nm. The violet portion of the visual spectrum is typically defined as spanning the range of about 380 to 450 nm. The light used may thus, e.g., have a wavelength of about 405 nm.

Light of these wavelengths is known to be very effective in killing any microbes that may have accumulated on the illuminated surfaces. The use of violet visible light for this particular implementation brings a number of advantages that are not found in UV or near UV light. For example, the low energy visible light does not damage the material of the surfaces it illuminates. This is especially advantageous because most domestic appliances, such as the air purifiers 100, 200, are at least partially made of plastics that are easily damaged by UV light. Another important advantage of the violet visible light is that no direct line of sight between the light source and the surface or part to be cleaned is needed. Indirect irradiation of the violet visible light helps to get rid of the microbial contamination too.

At least some nozzle cleaning LEDs 50 are arranged in such a way as to illuminate the nozzle 120, 220 of the air purifier 100, 200 for the decontamination thereof. This prevents the build-up of microbial contamination in and around the nozzles 120, 220 and the spreading of such contamination into the air together with the outgoing air 2 that is expelled therefrom. Filter cleaning LEDs 60 are arranged to illuminate the filters 140. Additional LEDs may be provided elsewhere along the air path through the devices 100, 200, in order to ensure that the air drawn through and expelled from the air purifiers 100, 200 picks up microbial contamination along the way. For example, airway cleaning LEDs 80 are provided close to the end of the air path for illuminating most of the end portion of that air path. Because this portion of the air path is close to the external environment of the air purifier 100, 200 and close to those parts of the device that may be touched by the user, possibly with a dishcloth full of bacteria, it has a higher risk of harbouring microbial contamination. With the airway cleaning LEDs 80 illuminating this area, such contamination can be eliminated before it gets a chance to grow and to be picked up by the outgoing air 2 that is expelled by the nozzle 120.

It is to be noted that emitting light in a violet portion of the visual spectrum as part of a decontamination process means that the emitted light contains a significant portion of light in that part of the electromagnetic spectrum and that the intensity of that significant portion is sufficient to have a useful anti-microbial and decontaminating effect. The emitted light does not need to be exclusively in the violet portion of the visual spectrum. As long as there is a sufficient intensity of light in that portion of the spectrum, and preferably at or around the 405 nm wavelength, for achieving a decontaminating effect, light of other parts of the electromagnetic spectrum may be emitted too. Further it is noted that, as part of the decontamination process, the intensity of the emitted light may vary over time. Such variations may be gradual and continuous or in the form of a pattern of light pulses. If pulsed light is used, the frequency, duration and intensity of the pulses may either be constant or varying.

In a simple embodiment, the LEDs 50, 60, 80 may be active whenever the air purifier 100, 200 is connected to an external power source. When the LEDs, 60, 80 only illuminate internal parts of the device 100, 200 and the light they emit is not visible from the outside, this may help to achieve optimal decontamination. However, if the emitted light is visible for the user, a time-controlled operation of the at least one light source may be preferred. For battery powered devices too, an always-on strategy may not be optimal. The air purifier may therefor comprise a controller 180, operatively coupled to and configured for timed control of the LEDs 50, 60, 80. While the controller 180 in the air purifier 100 of FIG. 2 is located on a printed circuit board provided inside the pedestal of the air purifier 100, at least part of its control functionality may be located remotely on a computer coupled to the air purifier 100 via a local or wide-area network. The controller 180 may, e.g., be configured to activate the LEDs 50, 60, 80 in response to activation of a decontamination button. The decontamination button may either be a physical button provided on the device 100, or a software representation of a button in a graphical user interface provided for controlling and monitoring the operation of the air purifier 100. Regardless of the button being implemented in hardware or software, it may be provided on a remote control or operable via a phone app or Internet website. The decontamination button allows the user to start and end the decontamination process at will. However, to ensure that the device 100 is decontaminated regularly, some form of automatic or semi-automatic control may be preferred.

In an exemplary embodiment, the controller 180 is operatively coupled to the compressor 130 and configured to activate the LEDs 50, 60, 80 during a decontamination period, a start and/or a duration of the decontamination period depending on an on/off state of the compressor 130. While the use of violet visible light is found to be an effective way to eliminate microbial contamination, it is a time-consuming process. When, e.g., using low intensity 405 nm LED light, illumination times of 30 minutes to a few hours may be needed for getting rid of most of the microbes. During use, the critical parts (nozzles 120, 220, filters 140, . . . ) are likely to be contaminated faster than the LEDs 50, 60, 80 can prevent. Decontaminating during use may therefore not be very useful or energy efficient. However, when the compressor is switched off, a decontamination program can start. A short delay may be built in to ensure that the air purifier 100, 200 is really not in use and not just switched off for a very short period of time.

If the air purifier 100 is battery powered, the LEDs 50, 60, 80 may be activated when the air purifier 100, 200 is connected to a battery charger. This avoids the battery pack being drained by the decontamination process and making it incapable of performing its primary function of purifying and expelling air. Activation and deactivation of the LEDs 50, 60, 80 may further depend on a charging state of the battery, for example by only activating the LEDs 50, 60, 80 when connected to the battery charger or when still being charged to at least 50% of its full battery capacity. Charging the battery pack may be done by simply connecting a power cable to a charger circuit. Alternatively, the batteries are charged when placing the air purifier 100, 200, or a battery containing part thereof, into a docking station that is provided for that purpose.

The air purifier 100, 200 may comprise a light guide, arranged to guide the emitted light from the LEDs 50, 60, 80 to the at least one nozzle 120, 220 or to any other to be decontaminated part. This may be especially useful in an air purifier 100, 200 with a plurality of nozzles 120, 220. For example, optical fibres or light guides of transparent or semi-transparent plastics may guide the emitted light from a central light source to the remotely located nozzles 120, 220, thereby obviating the need for separate light sources being provided with each nozzle 120, 220. The light guide may further help to illuminate other internal parts of the domestic appliance that may be susceptible to microbial contamination. For example, a large portion of the internal walls of the airway between the compressor 130 and the nozzle 120 may be equipped as a light guide, thereby reducing the risk of microbes growing inside the device 100, 200.

The use of light sources emitting light in a violet portion of the visual spectrum is equally useful in other domestic appliances that use a compressor to compress incoming air and to expel the compressed air through one or more nozzles. Examples of such domestic appliances are the hair dryer 300 shown in FIGS. 3 and 4 and the wearable air purifier 400 shown in FIGS. 5 to 9.

Figure 3:
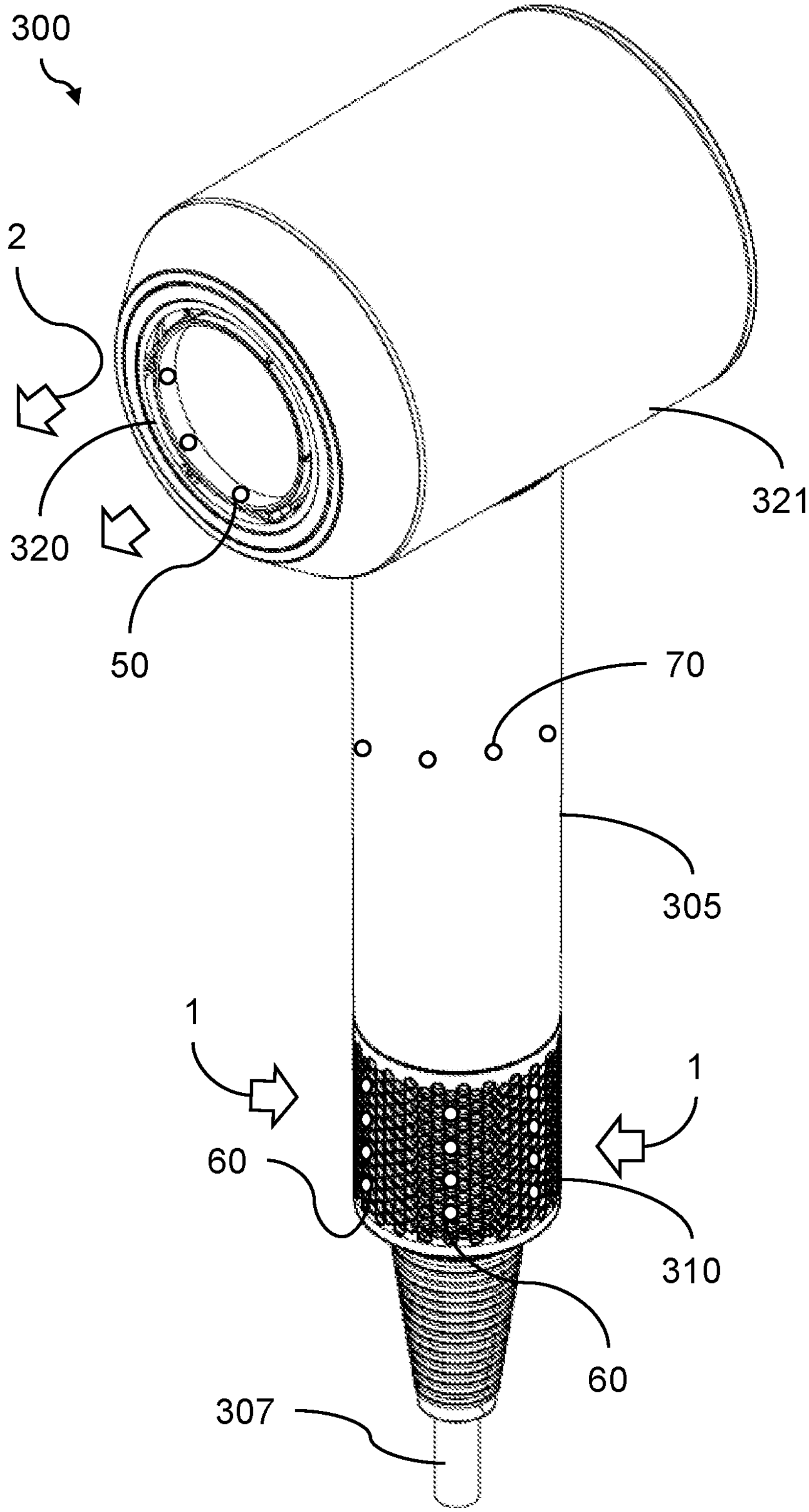
FIG. 3 shows a perspective view of a hair dryer according to the invention.
Figure 4:
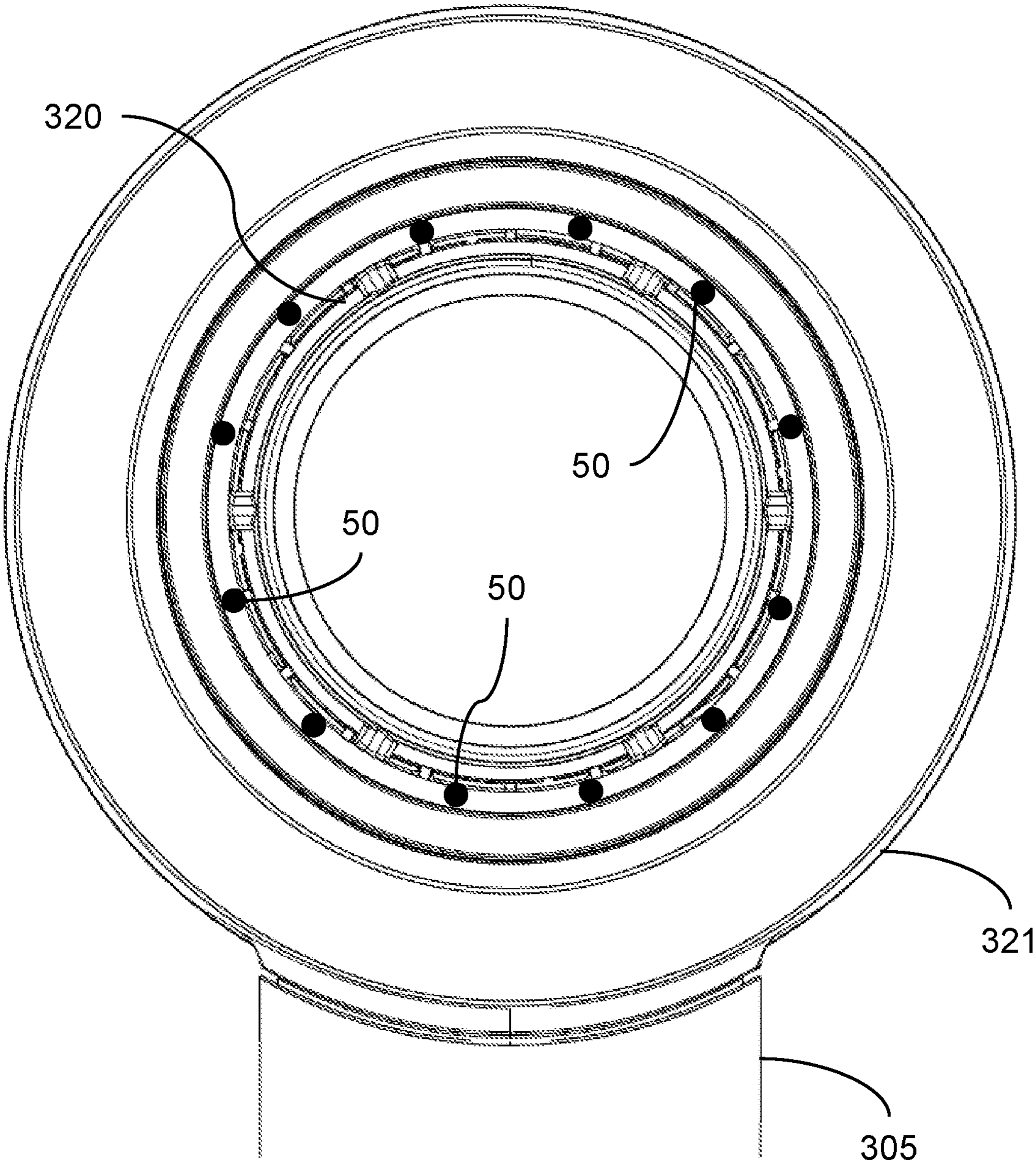
FIG. 4 shows a front view of part of the hair dryer of FIG. 3.

FIGS. 3 and 4 respectively show a perspective and a front view of a hair dryer 300 according to an embodiment of the invention. The hair dryer 300 comprises a compressor that is provided inside the stem or grip 305. When the compressor is operating, incoming air 1 is drawn inside through an air inlet 310 provided at the lower end of the grip 305. The compressor then compresses the air and expels it through an annular 320 nozzle at an end of a cylindrical head portion 321 of the hair dryer 300. The nozzle 320 may be provided as a single ring-shaped narrow opening or as a plurality of smaller nozzles installed in a circular configuration. In alternative embodiments, the nozzle 320 may have a shape that is not annular. The hair dryer 300 may be powered via a power cable 307 and/or by a battery embedded in the grip 305 or head portion 321 of the device.

Nozzle cleaning LEDs 50 for emitting light in a violet portion of the visual spectrum are provided in the vicinity of the nozzles 320 for enabling decontaminating the nozzles after use. The LEDs 50 may also emit the decontaminating light during use. However, because hair dryers 300 are typically only used for a few minutes per day, it is important to also use the LEDs 50 after use. Similarly, filter cleaning LEDs 60 for emitting light in a violet portion of the visual spectrum are provided near the air inlet 310 and/or near the filter units installed downstream the air inlet 302, inside the grip 305. These LEDs 60 ensure that air inlets and the filters are illuminated with the violet light and microbial contamination of those parts is minimised. Additional surface cleaning LEDs may be provided 70 on the grip 305 and/or under the head portion 321 to illuminate those portions of the hairdryer that are likely to be touched by the user.

Preferably, the operation of the LEDs 50, 60, 70 is controlled by a controller that may be provided inside the grip portion 305. For example, the LEDs 50, 60, 70 are turned on as soon as and while the power cable 307 is connected to an external power supply. The LEDs 50, 60, 70 may be turned off after a set amount of time of, for example, 30, 45 or 60 minutes. Preferably, the hair dryer 300, if powered through a power cable 307, comprises a battery for enabling powering the LEDs 50, 60, 70 when the power cable is unplugged. Such a battery, only provided for powering the LEDs and, possibly, an electronic controller and a graphical user interface can be much smaller and lighter than a battery that would be used for powering the compressor too.

It is noted that all aspects of the decontamination process described above for the air purifiers 100, 200 of FIGS. 1 and 2 are equally applicable to the hair dryer of FIGS. 3 and 4. The hair dryer 300 may, e.g., comprise internal light guides and its optional batteries may be charged using a docking station. Also, the same and similar control methods as described before may be used for controlling the LEDs 50, 60, 70 of the hair dryer.

Figure 5:
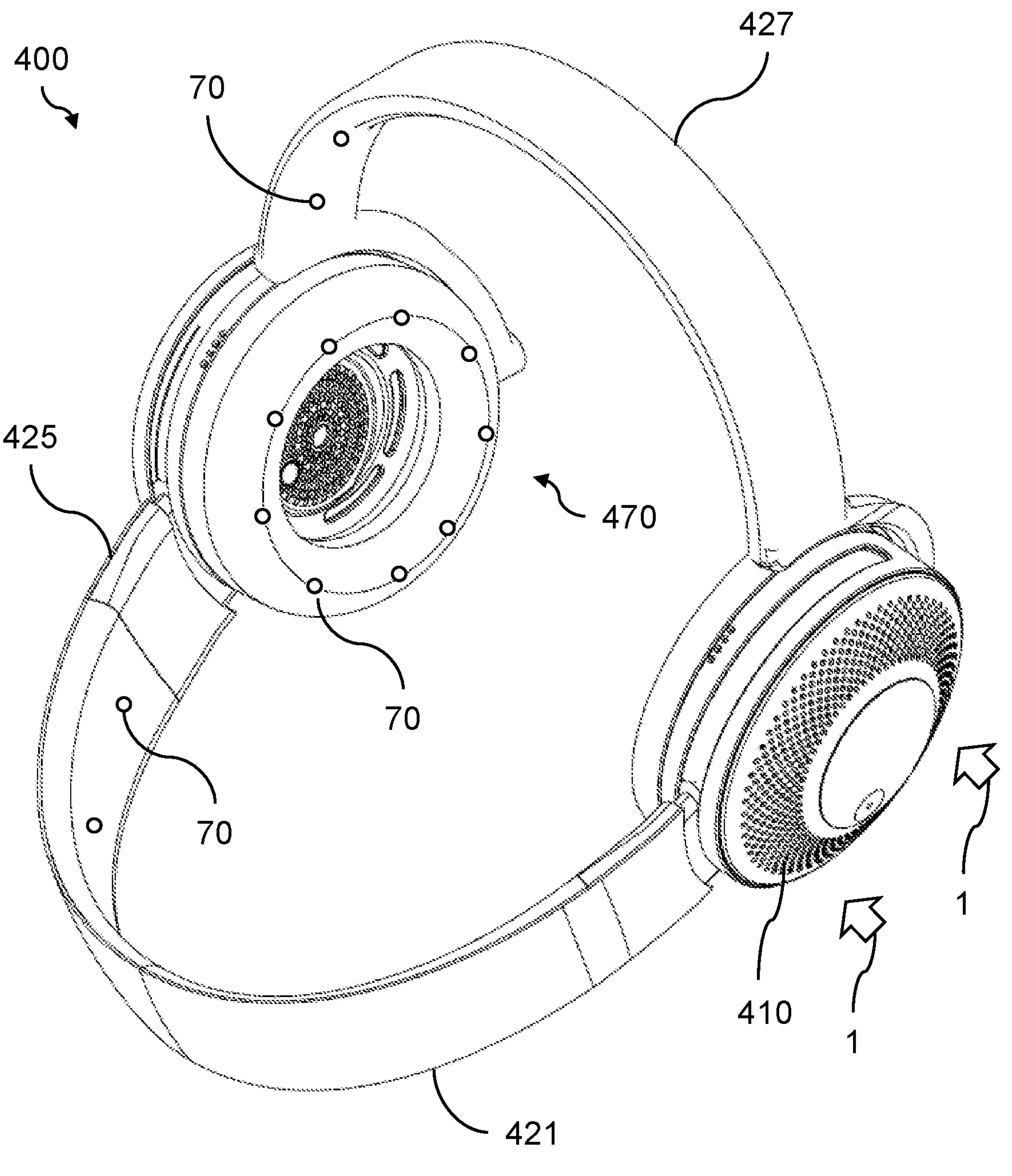
FIG. 5 shows a wearable air purifier according to the invention.
Figure 6:
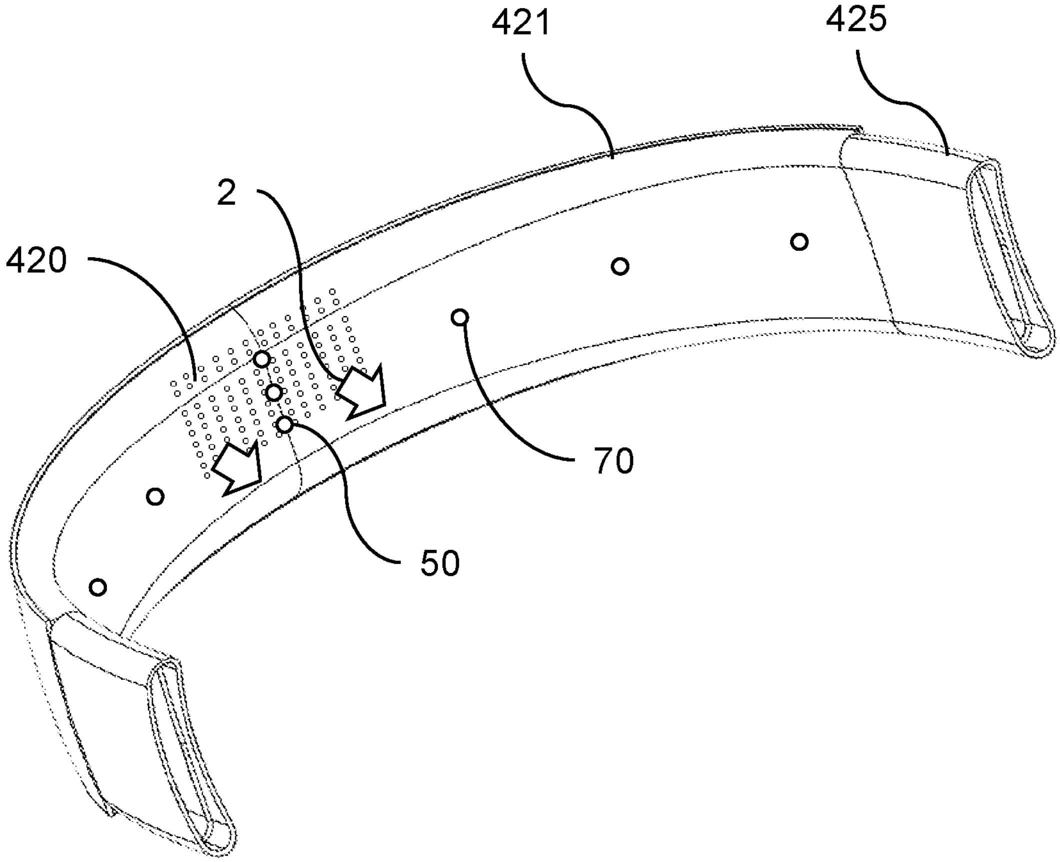
FIG. 6 shows the nozzle of the wearable air purifier of FIG. 5.
Figure 7:
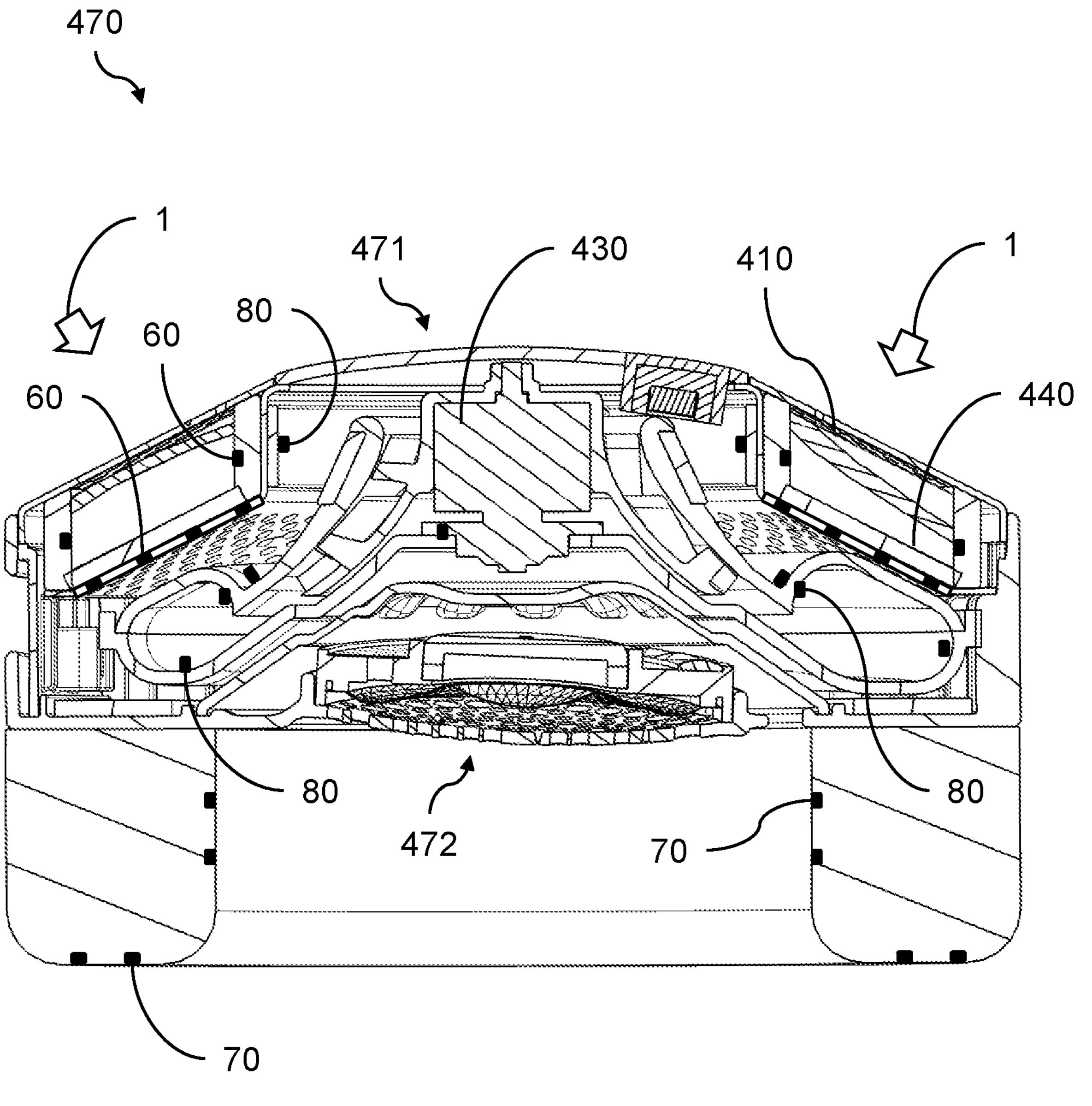
FIG. 7 shows a cross section of a speaker assembly of the wearable air purifier of FIG. 5.
Figure 8:
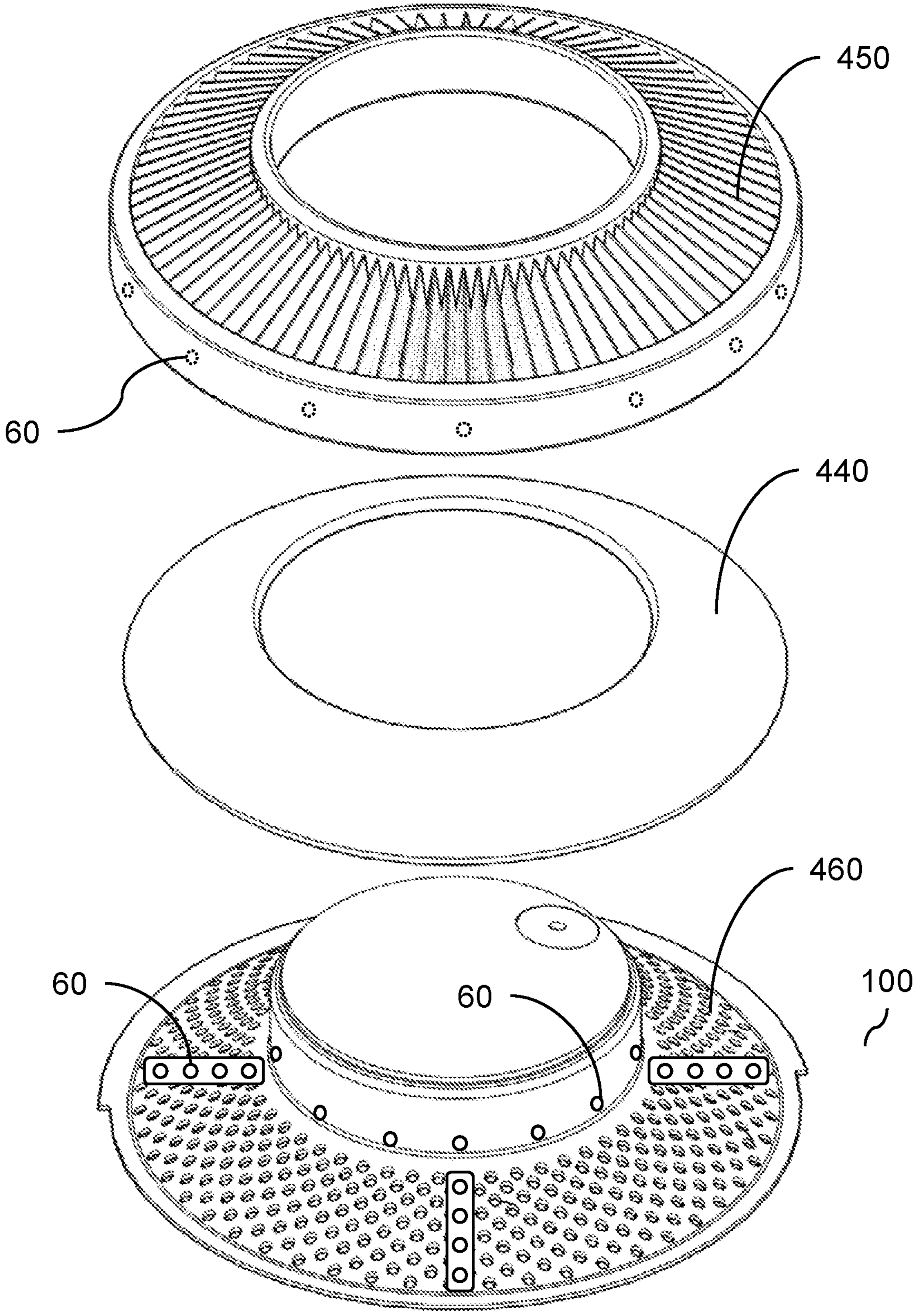
FIG. 8 shows an exploded view of part of some parts of the speaker assembly of FIG. 7.

FIG. 5 shows a wearable air purifier 400 according to the invention. FIG. 6 shows the nozzles 420 of the wearable air purifier 400 of FIG. 5. FIG. 7 shows a cross section of a speaker assembly 470 of the wearable air purifier 400 of FIG. 5. FIG. 8 shows an exploded view of part of some parts of the air purifier unit of the speaker assembly 470 of FIG. 7.

The wearable air purifier 400 is configured to be worn on a user's head, like a traditional set of headphones. The wearable air purifier 400 comprises two generally identical and cylindrical speaker assemblies 470 joint by an arcuate headband 427. The speaker assemblies 470 comprise a speaker unit 472 at the inside and a compact air purifier unit 471 at the outside. It is noted that the speaker unit 472 is not essential for the current invention. The speaker unit 472 comprises a speaker and speaker electronics. A Bluetooth or other type of wireless communication transmitter/receiver may be provided for wireless communication with an audio playing device. The speaker unit 472 and the air purifier unit 471 may share a battery pack and part of the control electronics.

The air purifier unit 471 comprises a compressor 430 for drawing in air 1 through the annular inlet 410 at the outer surface of the speaker assembly 470. The incoming air 1 is filtered by a filter 440 near the inlet 410 of the air purifier unit 471. The compressor 430 compresses the incoming air 1 that is then expelled from the speaker assembly 470 through the connector 425 that connects an arcuate mouthpiece 421 to the respective speaker assembly. The mouthpiece 421 has a plurality of nozzles 420 or outlets 420 through which the purified air is expelled from the device 400. Because, in use, the nozzles 420 are positioned just in front of the user's mouth, the user can brief in fresh purified air. Optionally, the mouthpiece can be disconnected or pivoted away when just using the speaker unit 472 and not the air purifier unit 471.

Like the domestic appliances 100, 200, 300 described above, the wearable air purifier 400 comprises various LEDs 50, 60, 70, 80 that emit light in a violet portion of the visual spectrum in order to decontaminate critical parts of the device 400. For example, one or more LEDs 50 are provided at or near the nozzles 420 for dealing with microbial contamination that may build up there. Especially if the same mouthpiece 421 is used by different users, it is important that any microbial contamination around the nozzles 420 is minimised. For the wearable air purifier 400 this is even more important than for the domestic appliances discussed above, because the user breathes out over the nozzles 420. These LEDs may, for example be provided in between, nozzles 420, around a group of nozzles 420, or behind the nozzles 420, inside the mouthpiece 421.

Surface cleaning LEDs 70 may be added to illuminate those parts of the mouthpiece 421 that do not include nozzles 420. When the wearable air purifier 400 is worn by the user, the light from these additional LEDs 70 illuminate their immediate surroundings. When the wearable air purifier 400 is not used, the light from these additional LEDs 70, not hindered by the face of the wearer, may illuminate larger parts of the mouthpiece 421. If pivoted away, the LEDs 50, 70 in the mouthpiece 4251 may illuminate the top of the arcuate headband 427. Similarly, additional LEDs 70 for decontaminating the outer surfaces of the wearable air purifier may be provided at the inside of the speaker assemblies 470. While these LEDs may be less useful when the user is wearing the device 400, they can decontaminate surfaces that were in direct contact with the user, e.g., while the batteries are being charged.

The cross section of FIG. 7 and the exploded view of FIG. 8 show how filter cleaning LEDs 60 may be provided for illuminating and thus decontaminating a filter 440 that is provided between the air inlet 410 and the airway leading to the compressor 430. Such filter cleaning LEDs 60 may be provided on the filter facing surfaces of a top and bottom part 450, 460 of a filter assembly comprising the filter 440. Additional airway cleaning LEDs 80 may be provided at various locations in the airways leading to and from the compressor 430. Although not shown, such airway cleaning LEDs may be provided inside the mouthpiece 421 too.

It is noted that all aspects of the decontamination process described above for the air purifiers 100, 200 and hair dryers 300 of FIGS. 1 to 4 are equally applicable to the wearable air purifier 400 of FIGS. 5 to 8. The wearable air purifier 400 may, e.g., comprise internal light guides and its batteries may be charged using a docking station. Also, the same and similar control methods as described before may be used for controlling the LEDs 50, 60, 70 of the wearable air purifier 400.

Figure 9:
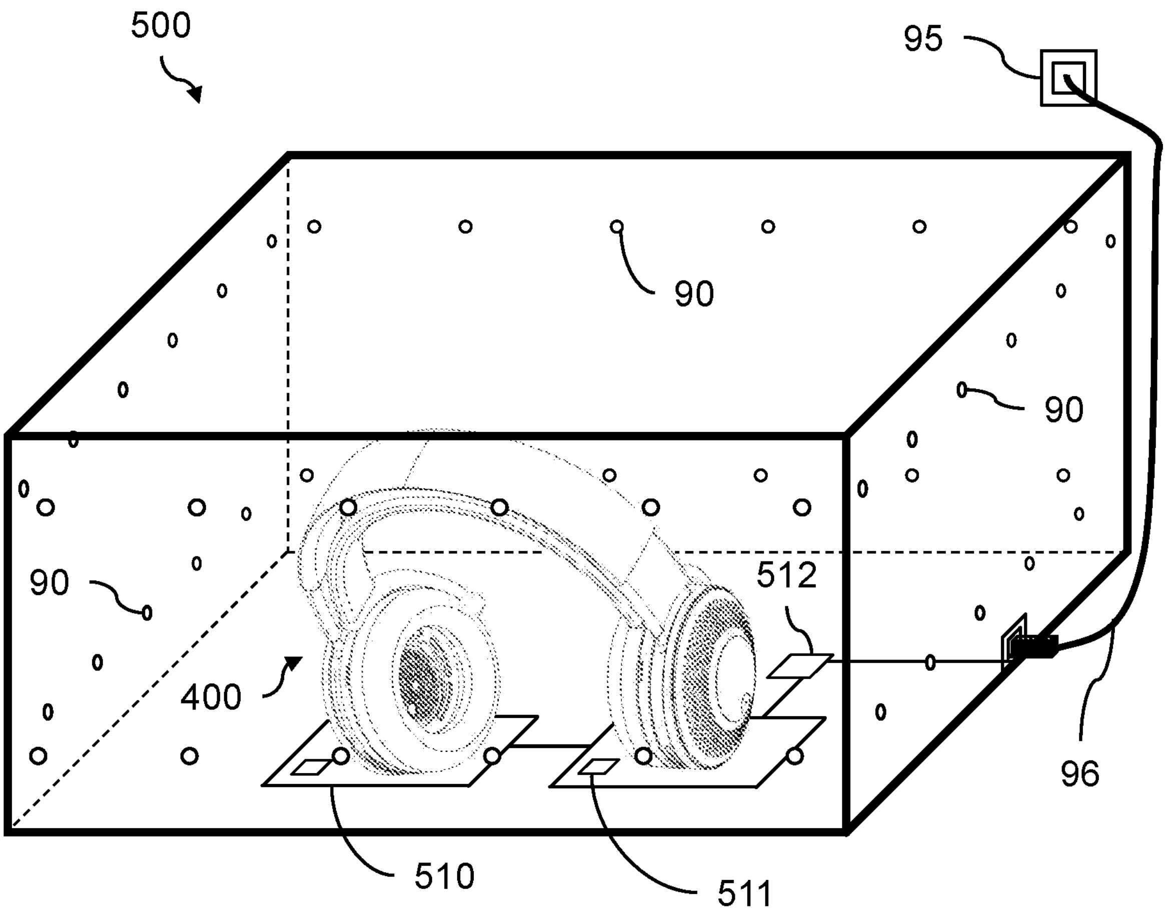
FIG. 9 shows a docking station for use with the wearable air purifier of FIGS. 5 to 8.

FIG. 9 shows a docking station 500 for use with the wearable air purifier 400 of FIGS. 5 to 8. It is, however, noted that the same or a similar docking station 500 may be used for other domestic appliances and/or for parts of domestic appliances too. For example, a nozzle portion or attachment piece of the hair dryer 300 may be decontaminated inside the docking station 500.

The docking station 500 comprises a docking bay 510 for receiving and holding the wearable air purifier 400. The docking bay 510 may comprise a docking sensor 511 for providing a docking signal when the wearable air purifier 400 is held in the docking bay 510. This docking sensor 511 may, for example, be a simple contact sensor or light sensor. The docking station 500 further comprises a plurality of LEDs 90 for emitting light in a violet portion of the visual spectrum. The LEDs are arranged in such a way as to illuminate substantially all sides of the wearable air purifier 400, but at least the nozzle portion 420 while the device 400 is being held in the docking bay 510. A docking station controller 512 is operatively coupled to the docking sensor 511 and the LEDs 90 and operative to receive the docking signal and to execute, in response thereto, a decontamination program. The decontamination program includes using the LEDs 90 to illuminate the parts to be cleaned.

The docking station 500 may be powered by an external power source such as a wall socket 95, via a power cable 96. Preferably, the docking station 500 is not only equipped for the decontamination of domestic appliances 100, 200, 300, 400 or parts thereof, but for charging of battery powered devices too. The amount of time needed for fully decontaminating the contaminated parts will generally be of the same order as the time needed for charging the batteries. When, e.g., using low intensity 405 nm LED light, illumination times of 30 minutes to a few hours may be needed for getting rid of most of the microbes. By integrating the charging and decontamination functionality in a single docking station 500, it is ensured that the decontamination process does not drain the batteries.

The docking station 500 may be designed to receive any domestic appliance as a complete unit or only separable parts of the device that need to be decontaminated or charged. The docking station 500 may comprise multiple docking bays 510 for receiving different parts and accessories of the device. For example, the docking station 500 may comprise a docking bay for a hair dryer that is charged and decontaminated when its presence is detected. A second docking bay may be provided for receiving an accessory comprising nozzles. The light sources 90 for illuminating the nozzles and other parts of the accessory may be switched on when the charging starts and/or when the placement of the accessory is detected. In another example, the docking station 500 is configured to receive a filter unit of, for example, an air purifier (wearable 400 or non-wearable 100, 200). The light source 90 is switched on when a presence of the filter unit is detected. Such a docking station 500 can be used for decontaminating the filter units of multiple air purifiers 100, 200, 400 owned by the same user.

In an embodiment, the docking station 500 further comprises a communication unit, operatively coupled to the docking station controller 512, for enabling communication between the docking station controller 512 and an appliance controller of the domestic appliance. Such a communication unit may, e.g., be used for receiving information from various sensors of the domestic appliance, or for receiving specific instructions from a controller of that device. Further, the communication unit may send similar sensor signals and/or instructions to the controller of the domestic appliance.

The invention has been described above in relation to a number of different embodiments. It is to be noted that the invention is equally applicable to other types of domestic appliances. Further, features used in and described with reference to specific embodiments are combinable with other embodiments. The scope of the invention is only limited by the following claims.

The invention claimed is:

1. A combination comprising:

a domestic appliance comprising an attachment, the attachment comprising an air outlet with at least one nozzle; and a docking station for the domestic appliance, the docking station comprising:

a docking bay for receiving and holding at least the attachment, the docking bay configured to surround all sides of the attachment of the domestic appliance, a docking sensor for providing a docking signal when the attachment of the domestic appliance is held in the docking bay, at least one light source for emitting light in a violet portion of the visual spectrum, the at least one light source being arranged in such a way as to illuminate the at least one nozzle by emitting the light while the attachment of the domestic appliance is being held in the docking bay, and a docking station controller, operatively coupled to the docking sensor and the at least one light source and operative to receive the docking signal and to execute, in response thereto, a decontamination program, the decontamination program including using the at least one light source to illuminate the at least one nozzle for the decontamination thereof, and wherein the docking station and the domestic appliance each comprise a communication unit for enabling communication between the docking station controller and an appliance controller of the domestic appliance.

2. The combination as claimed in claim 1, wherein the at least one light source is configured for emitting light with a wavelength of about 405 nm.

3. The combination as claimed in claim 1, wherein the domestic appliance comprises a light guide, arranged to guide the emitted light from the at least one light source to the at least one nozzle, the at least one nozzle being arranged within the attachment of the domestic appliance, and surrounded by all the sides of the attachment of the domestic appliance, and wherein the light guide comprises at least one of: an optical fiber, a transparent plastic, or a semi-transparent plastic.

4. The combination as claimed in claim 1, wherein the domestic appliance comprises a filter for filtering the incoming air, the at least one light source being arranged in such a way as to illuminate the filter.

5. The combination as claimed in claim 4, wherein the domestic appliance comprises a light guide, arranged to guide the emitted light from the at least one light source to the filter, the light guide comprising at least one of: an optical fiber, a transparent plastic, or a semi-transparent plastic.

6. The combination as claimed in claim 1, wherein the attachment of the domestic appliance comprises a light guide arranged to guide the emitted light from the at least one light source to an internal component of the attachment of the domestic appliance, the light guide comprising at least one of: an optical fiber, a transparent plastic, or a semi-transparent plastic.

7. The combination as claimed in claim 6, wherein the internal component is a filter.

8. The combination as claimed in claim 1, wherein the at least one light source comprises a plurality of LEDs.

9. The combination as claimed in claim 1, wherein the at least one light source comprises multiple light sources, each light source being arranged on each inner surface of the docking bay such that substantially all sides of the attachment of the domestic appliance are illuminated by the emitted light.

10. A system for docking at least a part of a domestic appliance, the system comprising:

the part of the domestic appliance, wherein the part of the domestic appliance comprises at least one light guide on an outer surface of the part, the at least one light guide comprising at least one of: an optical fiber, transparent plastic, or semi-transparent plastic; and a docking station at least for the part of the domestic appliance, the docking station comprising:

a docking bay for receiving and holding at least the part of the domestic appliance, a docking sensor for providing a docking signal when the part of the domestic appliance is held in the docking bay, at least one light source for emitting light in a violet portion of the visual spectrum, the at least one light source being arranged in such a way as to illuminate all outer sides of the part of the domestic appliance by emitting the light while the part of the domestic appliance is being held in the docking bay, and a docking station controller, operatively coupled to the docking sensor and the at least one light source and operative to receive the docking signal and to execute, in response thereto, a decontamination program, the decontamination program including using the at least one light source to illuminate the part of the domestic appliance for the decontamination thereof, wherein the light guide is arranged to guide emitted light from the at least one light source to an internal component of the part of the domestic appliance.

11. The system of claim 10, wherein the docking bay is configured to surround all of the outer sides of the part of the domestic appliance.

12. The system as claimed in claim 10, wherein the at least one light source comprises multiple light sources, each light source being arranged on each inner surface of the docking bay such that substantially all sides of the part of the domestic appliance are illuminated by the emitted light.

13. The system as claimed in claim 10, wherein the part comprises a nozzle.

14. The system as claimed in claim 10, wherein the internal component of the part of the domestic appliance is a nozzle.

15. The system of claim 10, wherein the part comprises an air outlet.

16. The system of claim 10, wherein the internal component is a filter.

17. The system of claim 10, wherein the part is an attachment, the domestic appliance comprising the attachment.

18. A combination comprising:

a domestic appliance comprising:

a filter for filtering incoming air, and a light guide, the light guide comprising at least one of: an optical fiber, a transparent plastic, or a semi-transparent plastic; and a docking station for the domestic appliance, the docking station comprising:

a docking bay for receiving and holding at least part of the domestic appliance, the docking bay configured to surround all sides of the at least part of the domestic appliance, a docking sensor for providing a docking signal when the at least part of the domestic appliance is held in the docking bay, at least one light source for emitting light in a violet portion of the visual spectrum, the at least one light source being arranged in such a way as to illuminate the filter by emitting the light while the at least part of the domestic appliance is being held in the docking bay, wherein the light guide of the domestic appliance is arranged to guide the emitted light from the at least one light source to the filter, and a docking station controller, operatively coupled to the docking sensor and the at least one light source and operative to receive the docking signal and to execute, in response thereto, a decontamination program, the decontamination program including using the at least one light source to illuminate the filter for the decontamination thereof.

19. The combination as claimed in claim 18, wherein the at least part of the domestic appliance comprises an air outlet with at least one nozzle.

20. The combination as claimed in claim 19, wherein the at least one light source is arranged in such a way as to illuminate the at least one nozzle by emitting the light while the at least part of the domestic appliance is being held in the docking bay, and wherein the decontamination program includes using the at least one light source to illuminate the at least one nozzle for the decontamination thereof.

* * * * *